US008859238B2

(12) United States Patent
Schneider et al.

(10) Patent No.: US 8,859,238 B2
(45) Date of Patent: Oct. 14, 2014

(54) METHOD FOR GENERATING A DOUBLE STRANDED NUCLEIC ACID WITH A SINGLE STRANDED OVERHANG

(75) Inventors: Uffe Vest Schneider, Valby (DK); Gorm Lisby, Vekso (DK)

(73) Assignee: Quantibact A/S, Hvidovre (DK)

( * ) Notice: Subject to any disclaimer, the term of this patent is extended or adjusted under 35 U.S.C. 154(b) by 0 days.

(21) Appl. No.: 13/695,228

(22) PCT Filed: May 6, 2011

(86) PCT No.: PCT/DK2011/050157
§ 371 (c)(1),
(2), (4) Date: Oct. 29, 2012

(87) PCT Pub. No.: WO2011/137911
PCT Pub. Date: Nov. 10, 2011

(65) Prior Publication Data
US 2013/0052652 A1  Feb. 28, 2013

(30) Foreign Application Priority Data

May 7, 2010 (DK) ................................ 2010 00403
Sep. 20, 2010 (DK) ................................ 2010 00843

(51) Int. Cl.
C12P 19/36 (2006.01)
C12Q 1/68 (2006.01)
C07H 21/02 (2006.01)
C07H 21/04 (2006.01)

(52) U.S. Cl.
USPC ........................... 435/91.1; 435/6.1; 435/91.2

(58) Field of Classification Search
USPC ................ 435/6.1, 91.1, 91.2; 536/23.1, 24.3
See application file for complete search history.

(56) References Cited

U.S. PATENT DOCUMENTS

| 5,525,494 A | 6/1996 | Newton |
| 8,501,441 B2 * | 8/2013 | Lisby ........................... 435/91.1 |
| 2009/0130657 A1 | 5/2009 | Millar |
| 2009/0136956 A1 | 5/2009 | Merante et al. |
| 2009/0216003 A1 | 8/2009 | Filichev et al. |

FOREIGN PATENT DOCUMENTS

| WO | WO-9421820 A1 | 9/1994 |
| WO | WO-0047766 A1 | 8/2000 |
| WO | WO 0060120 A2 * | 10/2000 |
| WO | WO-03/051901 A2 | 6/2003 |
| WO | WO-03/052133 A2 | 6/2003 |
| WO | WO-03/052134 A2 | 6/2003 |
| WO | WO-2006/125447 A2 | 11/2006 |
| WO | WO-2009/112032 A1 | 9/2009 |

OTHER PUBLICATIONS

Narayanan et al.; Clamping Down on Weak Terminal Base Pairs: Oligonucleotides with Molecular Caps as Fidelity-Enhancing Elements at 5' - and 3' - Terminal Residues; Nucleic Acids Research, 2004, vol. 32, No. 9, pp. 2901-2911.

(Continued)

Primary Examiner — Jezia Riley
(74) Attorney, Agent, or Firm — Edwards Wildman Palmer LLP; Jeffrey D. Hsi

(57) ABSTRACT

The present invention provides a method that combines the construction of double-stranded target amplification products with one or two single-stranded overhangs with improved production of such target amplification products. The single-stranded overhang(s) can be used for post-amplification capture and subsequent detection/manipulation. The single-stranded overhang(s) enable capture/detection/manipulation without interference from the complementary strand in the double-stranded target amplification product.

19 Claims, 6 Drawing Sheets

(56) References Cited

OTHER PUBLICATIONS

Brandal et al.; Octaplex PCR and Fluorescence-Based Capillary Electrophoresis for Identification of Human Diarrheagenic *Escherichia coli* and *Shigella* spp., Journal of Microbiological Methods, Feb. 2007; 68(2): pp. 331-341.

\* cited by examiner

Example 1: Bifunctional oligonucleotide (bfo)

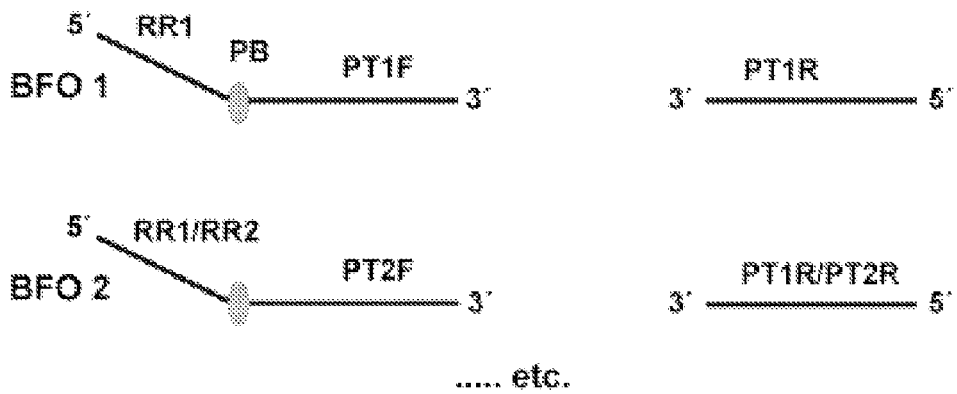
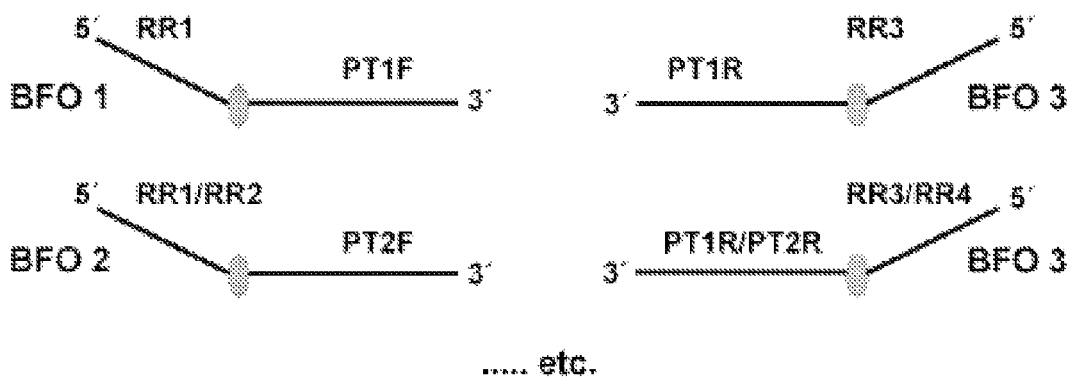
Fig. 3

A
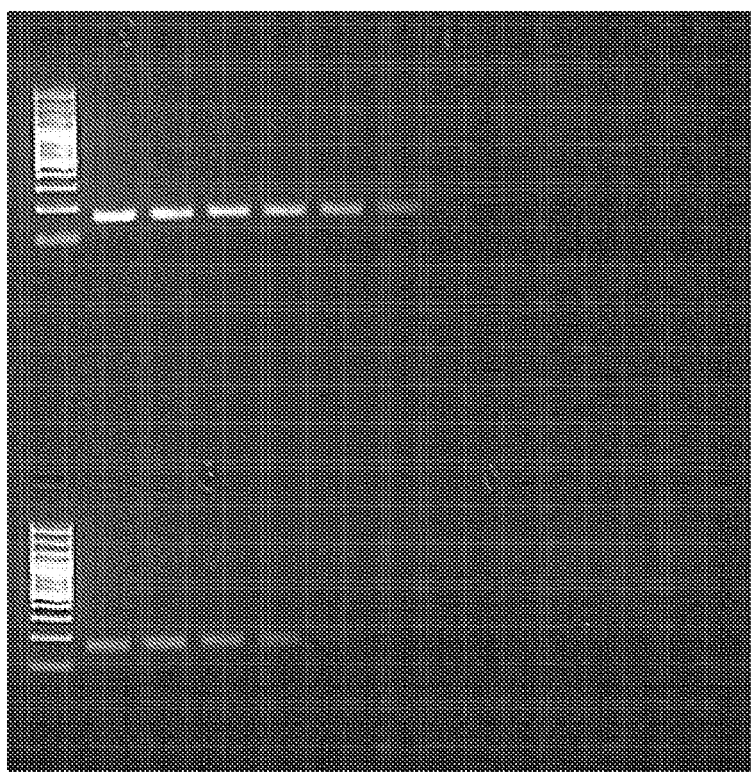
B
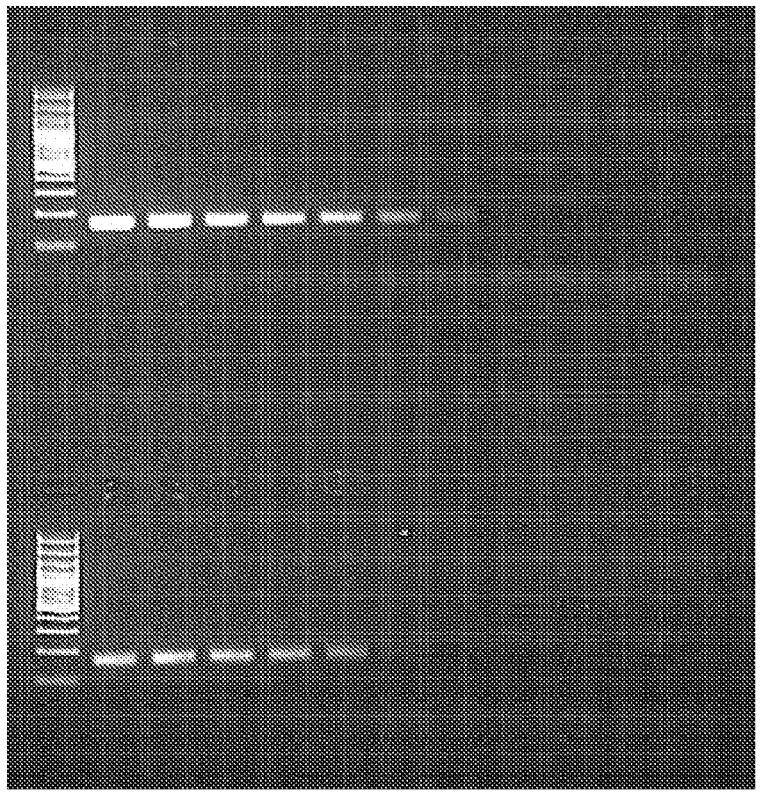
Fig. 4

A
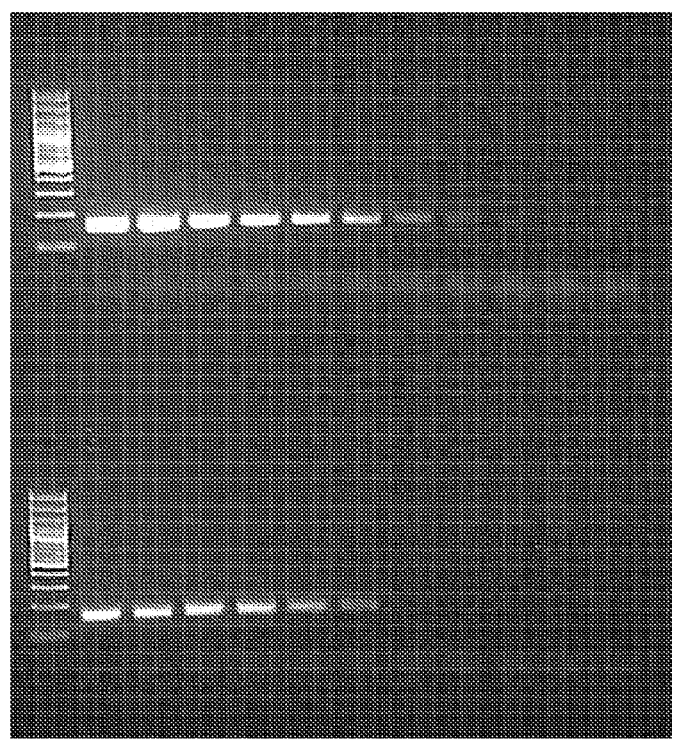
B
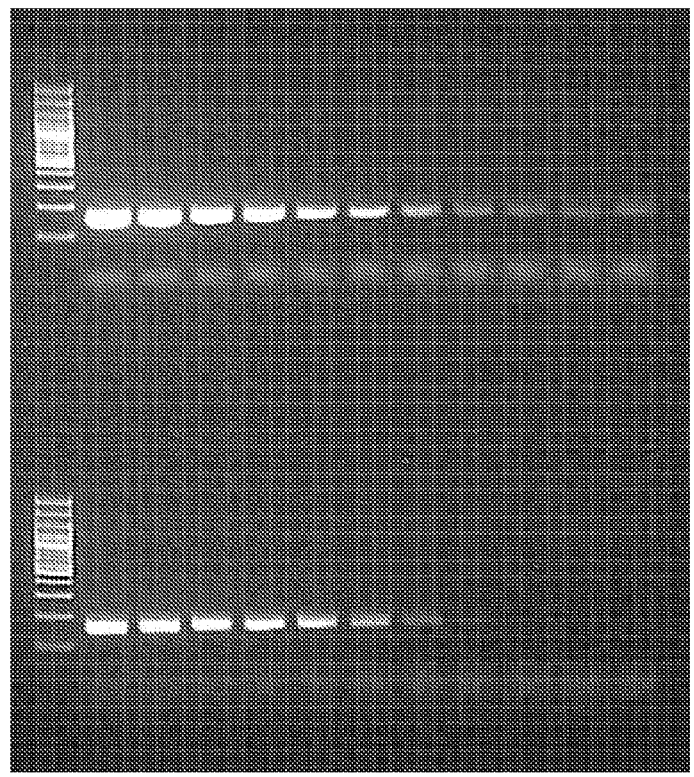
Fig. 5

METHOD FOR GENERATING A DOUBLE STRANDED NUCLEIC ACID WITH A SINGLE STRANDED OVERHANG

CROSS-REFERENCE TO RELATED APPLICATIONS

This application is the national phase under 35 U.S.C. §371 of PCT International Application No. PCT/DK2011/050157, filed May 6, 2011, which claims the benefit of Danish Patent Application No. PA 2010 00403, filed May 7, 2010, and Danish Patent Application No. PA 2010 00843, filed Sep. 20, 2010, the entire contents of the aforementioned applications are hereby incorporated herein by reference.

BACKGROUND OF THE INVENTION

In molecular biology and related fields, it is often desirable to make a double stranded nucleic acid such as a PCR product available for interaction with an oligonucleotide, e.g. a capture probe. This can e.g. be done by separating the two strands of the nucleic acid by increasing the temperature or by increasing the pH until the double stranded nucleic acid denatures. After denaturation, the capture probe may be added and the conditions reversed so that annealing of the capture probe can occur. However, if both strands are still present in the sample, they may renature and obviously compete with the capture probe. This of course decreases the efficiency of the capture process.

One solution is to physically separate the two strands of the nucleic acid before capturing one of the strands with the capture probe. However, this requires additional manipulations, which takes time and which may also lead to loss of material.

Thus, in PCR it would be advantageous to prevent the DNA polymerase from replicating all the way to the 3'end of the template, hence leaving single stranded 5'overhangs (as described in U.S. Pat. No. 5,525,494 (Zeneca Limited) 11. June 1996).

A common way of blocking the DNA polymerase, thus creating a single stranded overhang—but without the benefits on PCR efficacy and subsequent capture obtained by the present invention—is to insert a carbon linker between a PCR primer and a nonsense oligonucleotide sequence. The disadvantage compared to the present invention is the potential of the nonsense oligonucleotide sequence to flip-back onto the target nucleotide sequence due to the non-rigid structure of the carbon linker—thus interfering with the PCR polymerase. The carbon linkers can also coil-up and bring the nonsense oligonucleotide sequence and the primer sequence within close proximity allowing the PCR polymerase to read-through the linker. Such interference of the linker decreases subsequently the inter-assay uniformity of the multiplex PCR assay, and such interferences are not seen in present invention due to the rigid structure of the employed polymerase blocker.

WO9421820 describe a PCR method which uses primers with a non-replicable region to generate PCR products with single stranded overhangs (tails). The inventors used two non-base analogs (1,3 propanediol and 1,4-anhydro-2-deoxy-D-ribitol) in the PCR primers to prevent the polymerase from replicating all of nucleobases of the oligonucleotide used as primer, hence leaving a single stranded overhang corresponding to the nucleobases located at the 5'side of the non base analogs.

However, WO9421820 and U.S. Pat. No. 5,525,494 does not disclose polymerase blockers that benefit the PCR reaction in terms of specificity and sensitivity or that facilitate subsequent capture of the PCR product.

SUMMARY OF THE INVENTION

The present invention provides a method that combines the construction of double-stranded target amplification products with one or two single-stranded overhangs with improved production of such target amplification products. The single-stranded overhang(s) can be used for post-amplification capture and subsequent detection/manipulation. The single-stranded overhang(s) enable improved capture/detection/manipulation without interference from the complementary strand in the double-stranded target amplification product.

BRIEF DESCRIPTION OF THE FIGURES

FIG. 3:
Schematic drawing of multiplex PCR with primer sets of 1 (upper panel) and 2 bifunctional oligonucleotides.

FIG. 4A shows the ortho-TINA (row 1) and C3 spacer PCR (row 2) products at 50 nM on the annealing-gradient. See example 2 for details.

FIG. 4B shows the ortho-TINA (row 1) and C3 spacer PCR (row 2) products at 100 nM on the annealing-gradient. See example 2 for details.

FIG. 5A shows the ortho-TINA (row 1) and C3 spacer PCR (row 2) products at 200 nM on the annealing-gradient. See example 2 for details.

FIG. 5B shows the ortho-TINA (row 1) and C3 spacer PCR (row 2) products at 400 nM on the annealing-gradient. See example 2 for details.

DISCLOSURE OF THE INVENTION

Figure 1:
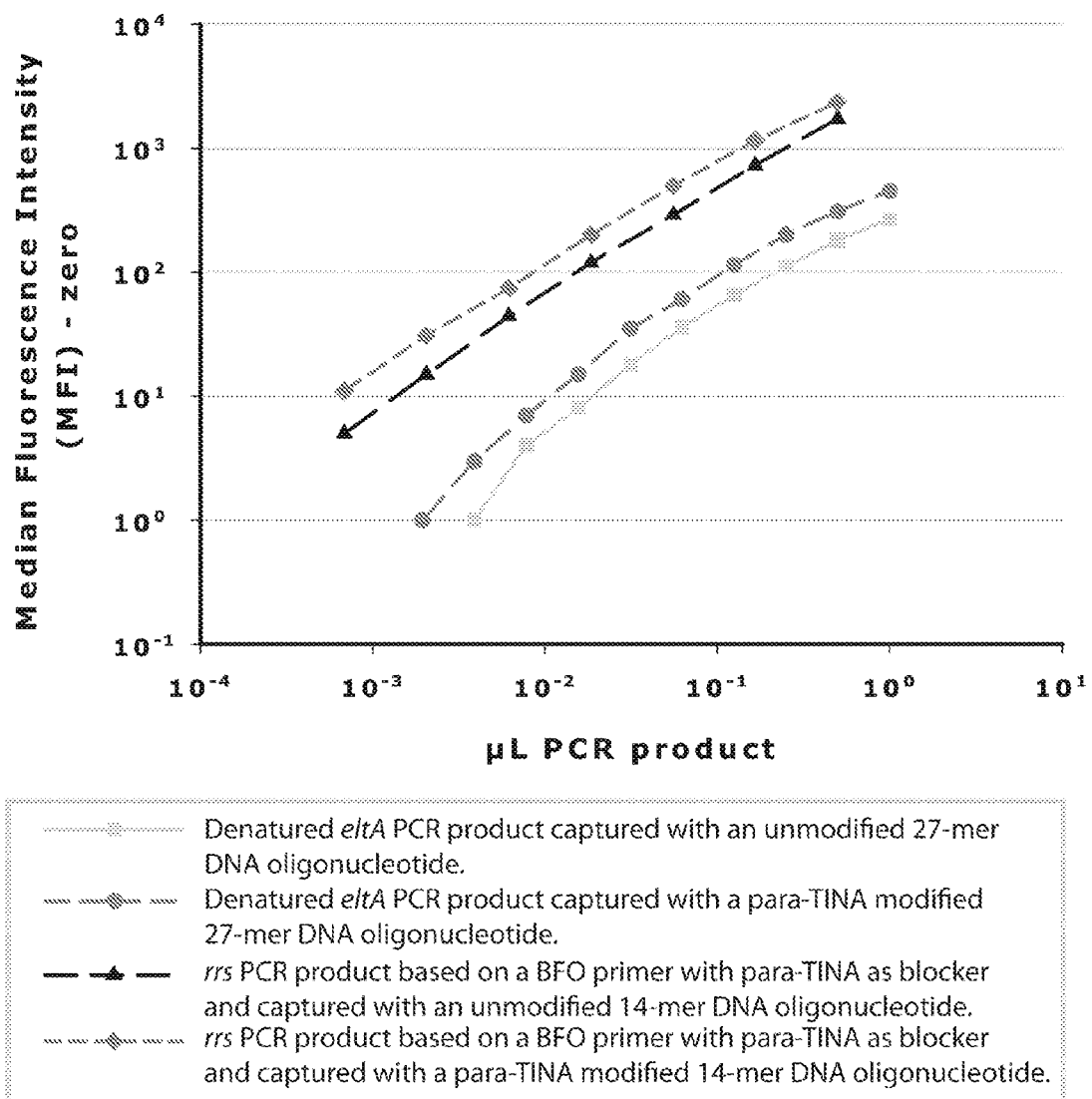
FIG. 1:
Detection of denatured PCR product or BFO modified PCR product as a function of the amount of PCR product. For both detection systems detection by DNA capture oligonucleotides and para-TINA modified DNA capture oligonucleotides are shown. See example 1 for more information.
Figure 2:
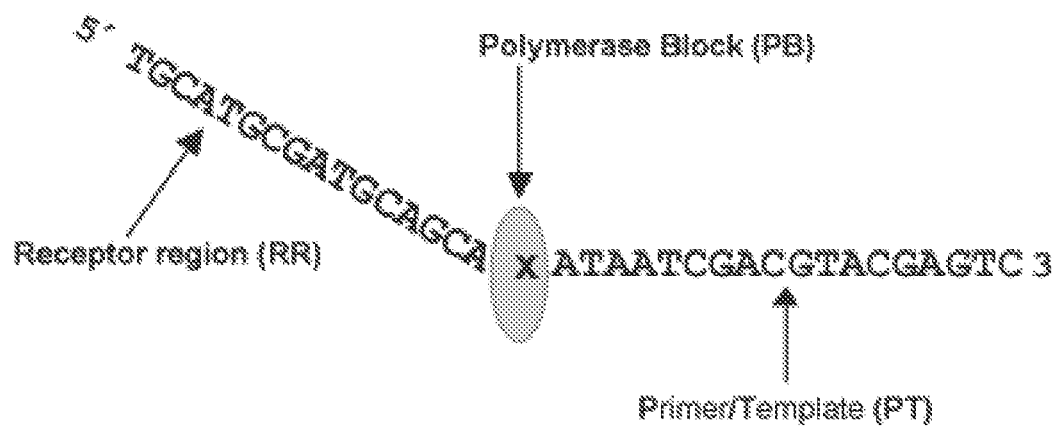
FIG. 2:
Schematic drawing of an exemplary bifunctional oligonucleotide as used in the present invention.

The present invention provides a method comprising the steps of:
a. Providing a template nucleic acid
b. Providing a bifunctional oligonucleotide (bfo) comprising a primer/template (pt) region (complementary to part of the template nucleic acid) in its 3'end and a capture region (cr), wherein the pt region and the cr region is separated by a polymerase block (B).
c. Mixing the components of steps a-b and providing conditions that allow the pt region of the bfo to anneal to the template nucleic acid
d. Under conditions allowing primer extension, extending the pt region of the bfo
e. Thereby generating a double stranded nucleic acid with a single stranded overhang (dso) corresponding to the cr region of the bfo In a preferred embodiment, the bfo of step b. is constructed as:

5'cr-B-pt 3'

In another embodiment, the bfo of step b. is constructed as:

X-B-pt 3'

Where "X" can be any combination of "cr", "B" and "pt". E.g. X=3'pt-B-cr 5'-B-5'cr (in which case the formula for this specific bfo will be: 3'pt-B-cr 5'-B-5'cr-B-pt 3'.

Preferably, extension in step d. is done as part of a reaction selected from the group consisting of: Exponential target amplification (e.g. Polymerase Chain Reaction (PCR), Ligase Chain Reaction (LCR), Rolling Circle Amplification), isothermal exponential target amplification (e.g. Nucleic Acid Sequence Based Amplification (NASBA), Strand Displacement Amplification (SDA), Transcription Mediated Amplification (TMA)), linear target amplification (e.g. Reverse Transcription, dideoxy sequencing).

In one embodiment, the template nucleic acid is RNA, wherefore the polymerase is a reverse transcriptase.

PCR

When the method is PCR, it will be recognized that the method further comprises the steps of:
f. Providing a second primer, which is complementary to the first extension product of step d
g. Denaturing the product of the step d
h. Under conditions allowing primer extension, extending the second primer annealed to the first extension product Steps f-h may be referred to as second strand synthesis.

In one embodiment, the second primer is also a bfo. Thus, the pt region of the second bfo primes second strand synthesis. The second bfo typically differs from the first bfo in the sequence of the pt region and/or the sequence of the cr region. As will be understood, also the length, content of nucleotide analogues and modified nucleotides, as well as the characteristics of the polymerase block may differ. When both the first and the second primer is a bfo, the double stranded product (amplicon) of the method has a single stranded overhang (capture regions) at both ends.

The polymerase is typically heat stable such that multiple repetitions of denaturation, annealing and extension can be performed. Otherwise, polymerase will have to be added after each denaturation step. Normally between 2 and 45, more preferably between 5 and 35 and most preferred between 10 and 30 repetitions are performed. As will be understood, the number of repetitions typically depends on the amount of template nucleic acid in the first cycle, the desired amount of end product as well as the efficiency of the process.

Multiplex

In the above described embodiment relating to PCR, two primers are used. Primer 1 is the bfo, primer 2 may be a bfo or may be a typical PCR primer. Either way, the two primers may be referred to as a primer set or primer pair that together enables amplification of a certain sequence to generate a PCR product (amplicon).

Instead of using just one primer pair, the method may employ multiple primer pairs such that the PCR reaction is a multiplex PCR. For primer set 2, one or both primers may be a bfo and so forth for additional primer sets.

In an embodiment, where only one of the primers in each primer set is a bfo, the capture region of the bfo of primer set 1 may be identical to the capture region of the bfo of primer set 2. I.e. the two amplicons may be captured by capture probes with identical sequences/moieties.

In a more preferred embodiment, the capture region of the bfo of primer set 1 is not identical the capture region of the bfo of primer set 2. I.e. the two amplicons may be captured by capture probes with different sequences/moieties, i.e. two separate areas on a solid surface (e.g. separate beads or onto separate locations on an array) and so forth for additional primer sets.

In another embodiment, where both primers in each primer set is a bfo, the capture region of the bfo used for subsequent capture of primer set 1 may be identical to the capture region of the bfo used for subsequent capture of primer set 2. I.e. the two amplicons may be captured by capture probes with identical sequences/moieties.

In a more preferred embodiment, the capture region of the bfo used for subsequent capture of primer set 1 is not identical the capture region of the bfo used for subsequent capture of primer set 2. I.e. the two amplicons may be captured by capture probes with different sequences/moieties, i.e. two separate areas on a solid surface (e.g. separate beads or onto separate locations on an array) and so forth for additional primer sets.

In this embodiment, where both primers in each primer set is a bfo, the capture region of the bfo used for subsequent detection/manipulation of primer set 1 may be identical to the capture region to the bfo used for subsequent detection/manipulation of primer set 2. I.e. the two amplicons may be detected/manipulated by probes with identical sequences/moities.

In a more preferred embodiment, the capture region of the bfo used for subsequent detection/manipulation of primer set 1 is not identical to the capture region of the bfo used for subsequent detection/manipulation of primer set 2. I.e. the two amplicons may be detected/manipulated by probes with different sequences/moieties, and so forth for additional primer sets.

The Bifunctional Oligonucleotide (bfo) for Use in the Method

The Primer/Template Region

Normally, the primer/template region of the bifunctional oligonucleotide consists entirely of natural nucleotides. Thus, it will most often consist exclusively of DNA monomers. In certain embodiments, it may also comprise a mix of DNA and RNA monomers or consist exclusively of RNA. In other embodiments, the primer/template region of the bfo may include one or more modified monomers/nucleic acid analogues/backbone modifications, as long as these still allow the pt region to be extended by a polymerase. Thus, in one embodiment it is preferred that first 2, 3, 4, 6, 8 or 10 nucleotides counting from the 3'end of the pt region are either unmodified DNA monomers or unmodified RNA monomers.

The length of the template/primer region of the bifunctional oligonucleotide is typically between 5 and 40 nucleotides in length, more preferred is a length between 8 and 30 and most preferred is a length between 10 and 25 nucleotides.

It should be recognized that template/primer does not necessarily have to be complementary to the template nucleic acid over its entire length. It may e.g. have additional sequences between the polymerase block and the region that is complementary to the template nucleic acid. Such additional sequences may e.g. comprise restriction sites.

The Capture Region.

It is preferred that the capture region is between 5 and 40 nucleotides in length, more preferred is a length between 8 and 30 and most preferred is a length between 10 and 25 nucleotides.

The capture region may comprise both natural nucleotides (unmodified DNA monomers and unmodified RNA monomers) and it may also comprise modified monomers and/or nucleotide analogues. The monomers may e.g. be modified at the sugar, and/or at the internucleotide linkage and/or at the base. Particular preferred monomers are 2-O-modified nucleotides such as 2-O-alkyl, 2-O-Flour, bicyclic nucleotides such as LNA (locked nucleic acid) and BNA, morpholino, FANA etc.

In one embodiment, the capture region may comprise or consist of PNA (peptide nucleic acid). In another embodiment, the capture region may consist only of nucleotide analogues and modified nucleotides that can be incorporated using standard oligonucleotide (phosphoroamidate) chemistry. In this embodiment, PNA is not used.

The capture region is typically oligonucleotide selected from the group consisting of: an aptamer and a single stranded capture sequence. The term aptamer as used herein refers to an oligonucleotide that adopts a three-dimensional structure and binds to a ligand by way of this structure (as opposed to binding via hybridization). Thus, the aptamer may have been evolved by SELEX to bind a certain protein. The aptamer may also bind an antibody, in which case the aptamer may be referred to as an epitope (antibody binding site).

In any of these cases, the capture region can interact with a ligand, e.g. a protein such as an antibody or a ligand in the form of a single stranded oligonucleotide capable of annealing to the capture region.

Other Functionalities of the bfo

The bfo(s) for use in the method of the invention may comprise additional functionalities. The bfo may e.g. comprise a release group, such as a cleavable linker, e.g. a disulfide bridge or a photocleavable moiety. The bfo may also comprise a capture group such as e.g. biotin. In one embodiment, the bfo comprise both a capture group and a release group. Also the other primer of the primer set (or sets) may comprise other functionalities.

Polymerase Block (B)

As to what is the primer/template region and what is the capture region of the bifunctional region, the primer/template region is easily distinguished from the capture region, because the primer/template region extends from the 3'end of the bfo to the first nucleotide or other moiety that does not allow further primer extension—when the bfo is used as template in an extension reaction, e.g. during PCR. Thus the first nucleotide or other moiety that does not allow further primer extension is the polymerase block, and the block may be one of the modified nucleotides or nucleotide analogues mentioned above.

It is preferred that the polymerase block is located at least 5, 6, 10, 12, 15, 18, 21, 24 or 27 nucleotides from the 3'end of template region of the primer/template region. Thus, in the corresponding embodiments, the primer/template region is therefore at least 5, 6, 10, 12 or 15, 18, 21, 24 or 27 nucleotides long.

The block (B) can be any moiety that—when incorporated into the backbone structure of a nucleic acid—will prevent the DNA or RNA polymerase from further extension when the block is encountered by the polymerase. The block is typically selected from the group consisting of nucleotide analogues, modified nucleotides, a linking moiety and an intercalator.

Nucleic analogues may e.g. be LNA, morpholino, FANA, HNA.

A preferred linking moiety is a polyalkylene glycol linker such as polyethylene glycol linker (PEG). Other linkers may also be used.

Intercalators

In one embodiment, it is preferred that the polymerase block comprise an intercalator, i.e. a moiety that can intercalate between the bases of DNA or RNA. Intercalators typically comprise aromatic ringsystems.

The intercalators to be used in the bfo may in principle be attached to the monomers of the bfo via a linker that allows intercalation or the intercalator may be included as an additional monomer.

In its broadest embodiments, such monomers may be described as:

X-L-I wherein X is a backbone monomer unit that can be incorporated into the backbone of a oligonucleotide or a oligonucleotide analogue, or PNA, or PNA analogues, L is a linker, $I_1$ is a first intercalator comprising at least one essentially flat conjugated system, which is capable of co-stacking with nucleobases of DNA, RNA or analogues thereof.

Preferably, the backbone monomer unit X comprises alkylendiol, such as ethylenglycol or 1-O-methyleneglycerol which optionally has the alkylenediol partly comprised in a ring system, such as glycon. For example, the backbone monomer X may be a part of four, five or six member rings which eventually have heteroatoms selected from nitrogen, sulphur, phosphorous, and oxygen. Preferably, the alkylenediol directly links neighbouring monomer units of the oligonucleotide, and it is to be understood that in this embodiment, the alkylenediol may still be part of a ring system such as e.g. glycon.

In one embodiment, the linker L of the monomer comprises 0-60 atoms.

In another embodiment, L comprises a chain or a ring or combinations thereof and/or substitutions thereof.

In still another embodiment, L comprises an alkyl chain or an oxaalkyl chain or an azaalkyl chain or a thiaalkyl chain or a carboxamide group or an thiocarboxamide group or an sulphonamide group or combinations thereof.

In a preferred embodiment, the unit length of the backbone monomer unit X including a phosphorous atom is less than 6 atoms, wherein the backbone unit length is the shortest distance from one monomer to the next.

Preferred intercalators for use as block that is added as an additional monomers can be selected from the group consisting of a TINA monomer as described in WO/2006/125447 (hereby incorporated by reference), an INA monomer as described WO/2003/052134 and WO/2003/052133, WO/2003/051901 (hereby incorporated by reference), 5'-appended acylamido caps as described in Narayanan S et al, NAR 2004, 32: 2901-2911 (hereby incorporated by reference),

TINA

TINA (twisted intercalating nucleic acid) have been found to be particular favorable for certain applications of the bfo, because it seems to direct the capture region away from the primer/template region monomers. Thus, the capture region will have little tendency to interact with the primer/template region when a TINA monomer is used as block.

The TINA monomer may be described by the general structure Z:

X-L-I-C-$I_2$ wherein X is a backbone monomer unit that can be incorporated into the backbone of a oligonucleotide or a oligonucleotide analogue, or PNA, or PNA analogues, L is a linker, $I_1$ is a first intercalator comprising at least one essentially flat conjugated system, which is capable of co-stacking with nucleobases of DNA, RNA or analogues thereof, C is an optional conjugator and $I_2$ is a second intercalator comprising at least one essentially flat conjugated system, which is capable of co-stacking with nucleobases of DNA, RNA or analogues thereof.

In a preferred embodiment, the backbone X is capable of being incorporated into a oligonucleotide of DNA, RNA, HNA, MNA, ANA, LNA, CAN, INA, CeNA, TNA, (2'-NH)-TNA, (3'-NH)-TNA, α-L-Ribo-LNA, α-L-Xylo-LNA, β-D-Ribo-LNA, β-D-Xylo-LNA, [3.2.1]-LNA, Bicyclo-DNA, 6-Amino-Bicyclo-DNA, 5-epi-Bicyclo-DNA, α-Bicyclo-DNA, Tricyclo-DNA, Bicyclo[4.3.0]-DNA, Bicyclo[3.2.1]-DNA, Bicyclo[4.3.0]amide-DNA, β-D-Ribopyranosyl-NA, α-L-Lyxopyranosyl-NA, 2'-R-RNA, 2'-OR-RNA, 2'-AE-RNA, α-L-RNA, β-D-RNA, and combinations and modifications thereof.

In another embodiment, the backbone monomer unit X comprises alkylendiol, such as ethylenglycol or 1-O-methyleneglycerol which optionally has the alkylenediol partly comprised in a ring system, such as glycon. For example, the backbone monomer X may be a part of four, five or six member rings which eventually have heteroatoms selected from nitrogen, sulphur, phosphorous, and oxygen. Preferably, the alkylenediol directly links neighbouring monomer units of the oligonucleotide, and it is to be understood that in this embodiment, the alkylenediol may still be part of a ring system such as e.g. glycon.

In one embodiment, the linker L of the flexible basestacking monomer comprises 0-60 atoms.

In another embodiment, L comprises a chain or a ring or combinations thereof and/or substitutions thereof.

In still another embodiment, L comprises an alkyl chain or an oxaalkyl chain or an azaalkyl chain or a thiaalkyl chain or a carboxamide group or an thiocarboxamide group or an sulphonamide group or combinations thereof.

In a preferred embodiment, $I_1$ is a monocyclic or polycyclic aromatic ringsystem optionally selected from the group of a benzene, naphthalene, azulene, bicyclic heteroaromatic ring systems and substitutions thereof.

In a preferred embodiment, $I_1$ is positioned with L and C in position 1,2 of the monocyclic or polycyclic aromatic ringsystem.

In yet another embodiment, $I_1$ is positioned with L and C in position 1,3 of the monocyclic or polycyclic aromatic ringsystem, In another embodiment, $I_1$ is positioned with L and C in position 1,4 of the monocyclic or polycyclic aromatic ringsystem, In a more preferred embodiment is $I_1$ a benzene ring with L and C in an ortho (L and C in position 1,2)- or para-position (L and C in position 1,4).

C of the flexible basestacking monomer is an optional conjugator. In a preferred embodiment where C is non-optional, C is selected from the group of an alkyl of from 1 to 12 carbons, alkenyl of from 2 to 12 carbons, alkynyl 2 to 25 carbons or diazo or combinations thereof with a length of no more than 25 carbons or/and nitrogen atoms.

In an alternative embodiment the flexible basestacking monomer does not contain any conjugator. Thus, $I_1$ and $I_2$ may be linked directly e.g. via a conjugated system.

In another embodiment, C is selected from the group consisting of straight-chain or branched-chain or monocyclic aromatic rings and substitutions thereof which eventually have heteroatoms selected from nitrogen, sulphur, phosphorous, and oxygen.

In still another embodiment, the alkenyl of C is an acetylene or repetitive acetylenes.

In a preferred embodiment, the unit length of the backbone monomer unit X including a phosphorous atom is less than 6 atoms, wherein the backbone unit length is the shortest distance from one monomer to the next.

In a preferred embodiment, the linking moiety L has a length of at least 2 atoms and eventually possesses heteroatoms selected from nitrogen, sulphur, phosphorous, and oxygen. Preferably, the linking moiety L has a length between 2 and 10 atoms, more between 2 and 5 atoms. In a most preferred embodiment, the linking moiety has a length of 3 atoms corresponding to 5 bonds between X and $I_1$.

$I_2$ of the flexible basestacking monomer is a second intercalator comprising at least one essentially flat conjugated system, which is capable of co-stacking with nucleobases of DNA, RNA or analogues thereof.

In a preferred embodiment, $I_2$ is selected from the group of bi-cyclic aromatic ringsystems, tricyclic aromatic ringsystems, tetracyclic aromatic ringsystems, pentacyclic aromatic ringsystems and heteroaromatic analogues thereof and substitutions thereof. Most preferred are tetracyclic ringsystems and in particular pyrene.

In a particular embodiment $I_2$ is a 1H-phenanthro[9,10-d]imidazol-2-yl group or pyrene In a most preferred embodiment Z can be described by the formula:

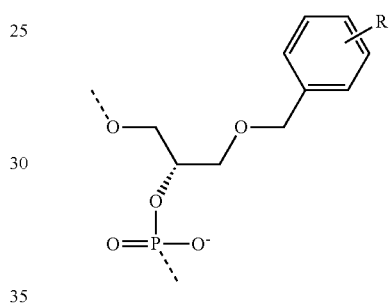

wherein R is selected from the group of arylethynyl, pyreneethynyl, and 1H-phenanthro[9,10-d]imidazol-2-yl and group R may be substituted in the ortho, meta or para position of benzene. More preferred are the ortho and para positions.

INA

INA (intercalating nucleic acid) may be described by the general formula

X—Y-Q

Wherein X is a backbone monomer unit capable of being incorporated into the backbone of a nucleic acid or nucleic acid analogue, preferably X comprises alkylenediol.

Q is an intercalator comprising at least one essentially flat conjugated system, which is capable of co-stacking with nucleobase of DNA, preferably Q is a from the monocyclic or a polycyclic aromatic ringsystem selected from the group consisting of benzene, naphthalene, azulene and bicyclic heteroaromatic ring systems, tricyclic aromatic ringsystems, tetracyclic aromatic ringsystems, pentacyclic aromatic ringsystems and heteroaromatic analogues thereof and substitutions thereof. Most preferred is tetracyclic ringsystems and in particular pyrene.

Y is a linker moiety linking said backbone monomer unit and said intercalator.

The total length of Q and Y is typically between 5 and 25 Å, more preferably between 7 and 20 Å.

In a preferred embodiment, the unit length of the backbone monomer unit X including a phosphorous atom is less than 6 atoms, wherein the backbone unit length is the shortest distance from one monomer to the next.

Capture Region—Ligand Interactions

The double stranded nucleic acid comprising one or two single stranded overhangs (capture regions) is typically subjected to further manipulations, preferably, where the capture region (cr) of the dso interacts with a ligand, e.g. an oligonucleotide or a protein.

Nano-Structures

Thus, the double stranded nucleic acid may e.g. be used in nano-technology for the generation of nucleic acid-based nano-structures. In such an embodiment, the double stranded nucleic acid with single stranded overhand is typically contacted with a second double stranded nucleic, preferably also a double stranded nucleic acid with single stranded overhang. The single stranded overhangs are typically designed such that they have complementary regions, i.e. the can anneal to each other. One single stranded overhang may have a length that allows annealing to more than one other single stranded overhang, e.g. 2 or 3. In this way, rigid double stranded nucleic acids can be connected in a various ways to build nanostructures.

Capture

In another embodiment, the method further comprises a capture step, wherein capture region (cr) of the dso is annealed to a capture probe. The polymerase block B used in the present invention, e.g. TINA described above, improves capture as shown in example 1. Not intended to be bound be theory, it is believed that improved capture is based on the rigid TINA structure, which directs the capture region away from the double stranded region and hence increases accessibility of the capture region.

The capture probe is usually immobilized in a solid support or alternatively the capture probe is adapted for immobilization on a solid support.

The solid support may e.g. be a bead, blot or an array.

After the dso has been contacted with the capture probe and the capture probe annealed to the cr, a fractionation step is typically performed to separate annealed molecules (PCR products) from non-annealed molecules.

In a preferred embodiment, the capture probe comprises an intercalator, e.g. a TINA monomer or an INA monomer as described above. The capture probe may also comprise 2 or more intercalators. As shown in the examples section, a capture probe comprising an intercalator improves the efficiency of the capture reaction.

When the target amplification product has been captured on a solid surface, the next step will typically be one or more of the following:
 a. a detection phase, whereby the immobilized target amplification product is visualized
 b. a purification phase, whereby the immobilized target amplification product is purified
 c. a manipulation phase, whereby the immobilized target amplification product is further manipulated.

EXAMPLES

Introduction

In the method of the invention, a polymerase block such as e.g. a TINA molecule is placed in a bifunctional oligonucleotide. The part of the oligonucleotide 3' to the TINA molecule functions as a conventional PCR primer, whereas the part of the oligonucleotide 5' to the TINA molecule is a nonsense oligonucleotide tail. This approach has multiple advantages, which can be summarized in i) increased multiplex PCR efficacy, ii) improved analytical sensitivity upon detection of multiplex PCR reactions, iii) decreased nonspecific cross-reactivity in microarray and biosensor approaches for detection of multiplex PCR products and iv) easier design and more uniform PCR reactions. The TINA molecule in the bifunctional oligonucleotide still improves the efficacy of the PCR reaction, but the TINA molecule also eliminates read-through by the PCR polymerase, leaving the nonsense oligonucleotide sequence as a single stranded overhang. The single stranded PCR overhangs, allow detection of the multiplex PCR reaction without preceding denaturation of PCR products—increasing the analytical sensitivity of the detection of PCR amplicons. The risk of cross-reactivity between multiple PCR amplicons is diminished, since the nonsense oligonucleotide tag-sequence can freely be designed. As the PCR amplicons are discriminated by the nonsense oligonucleotide tag-sequence, the PCR amplicons can be designed with similar lengths. By equaling the lengths of the PCR amplicons, uniformized multiplex PCR efficacy can be achieved—simplifying the optimization of the multiplex PCR assay. A final benefit of the method of the invention is a greater inter-assay uniformity of the multiplex PCR assay.

Example 1

The objective of the experiment was to compare solid phase detection of denatured PCR product with detection of BFO modified PCR product.

PCR Reactions:

A primer set targeting the eltA gene from E. coli was chosen for conventional PCR, whereas a primer set targeting the rrs gene was used for BFO modified PCR. The sequences for both primer sets were based on Brandal L T et al, J Microbiol Methods. 2007 February; 68(2):331-41. All oligonucleotides in the example were purchased from IBA GmbH or DNA Technology A/S on a 0.2 μmol synthesis scale with HPLC purification and quality control.

A clinical ETEC E. coli strain D2262 (estA, eltA and rrs positive) was grown on a SOS plate at 37° C. overnight. Half a colony was dissolved in 100 μL water and cells were lysed at 95° C. for 15 minutes. Cell debris was removed by centrifugation at 2300 g for one minute and the supernatant was used for PCR.

The primer pair for conventional PCR on the eltA gene was

| Name: | Sequence: |
|---|---|
| eltA TAG17 F | AAGAGAAGGAGAAAGAGTCTCTATGTGCATACGGAGC |
| eltA Bio R | Biotin-CCATACTGATTGCCGCAAT |

PCR fragment length: 322 bp.

The primer pair for bifunctional oligonucleotide PCR on the rrs gene was

| Name: | Sequence: |
|---|---|
| rrs T-TAG17 F | AGAGGAAGAAGAGAGAAXCCCCCTGGACGAAGACTGAC |
| rrs Bio R | Biotin-ACCGCTGGCAACAAAGGATA |

PCR fragment length 401 bp.

X equals para-TINA (Z as described on page 13 wherein R is pyreneethynyl, which is substituted in the para position of benzene) and biotin is a standard biotin.

PCR was performed in a reaction volumen of 25 μL with 1×PCR buffer (1.61 g/L Tris-HCl, 6.88 g/L Trizma-base, 2.12 g/L $(NH_4)_2SO_4$, 100 μL/L Tween 80, 5 g/L Ficoll 400), 0.2 mM of each dNTP, 0.2 μM of each primer, 2.5 mM MgCl$_2$, 0.08% BSA, 1 μL template DNA and 1 U KAPA2GO Robust HS DNA polymerase. The PCR was run on a SensoQuest Labcycler using a PCR program consisting of step 1: 95° C. for 4 minutes; step 2: 30 cycles of step 3 to 5; step 3: 95.0° C. for 15 seconds; step 4: Y° C. for 30 seconds; 5: 72.0° C. for 30 seconds and step 6: 72° C. for 1 minute. Y was 59.5° C. for the eltA PCR and 53.1° C. for the rrs PCR. The PCR products were purified using the MN Nucleospin Extract II kit from Macherey-Nagel. DNA concentrations were measured on a Nanodrop™ and were 18.3 ng/μL for the eltA PCR reaction and 42.4 ng/μL for the rrs PCR reaction.

Luminex Detection of BFO Modified PCR Product:

The BFO modified rrs PCR product was detected on the Luminex200™ using capture oligonucleotides coupled to a set of three magnetic beads (MagPlex™) targeting eltA, estA and rrs in each well. Capture oligonucleotides for estA were coupled to bead 15, rrs to bead 29 and eltA to bead 61. The single stranded overhangs of the BFO modified PCR products were captured by Watson-Crick based antiparallel duplex formation to conventional DNA or para-TINA modified DNA oligonucleotides.

| Capture oligo name: | Capture oligo sequence: |
|---|---|
| C_estA_AD_008 | NH2-CX-HEGL-TTTCCTCTTCCTTT |
| C_rrs_AD_008 | NH2-CX-HEGL-TCTCTTCTTCCTCT |
| C_eltA_AD_008 | NH2-CX-HEGL-TTTCTCCTTCTCTT |
| C_estA_AD_010 | NH2-CX-HEGL-XTTTCCTCTTCCTTTX |
| C_rrs_AD_010 | NH2-CX-HEGL-XTCTCTTCTTCCTCTX |
| C_eltA_AD_010 | NH2-CX-HEGL-XTTTCTCCTTCTCTTX |

X equals para-TINA, NH2-CX equals an aminomodified cyclohexan spacer and HEGL equals a C18 hexaethyleneglycol spacer.

Conventional DNA capture oligonucleotides were coupled using a EDC based coupling procedure as recommended by Luminex, whereas para-TINA modified oligonucleotides were coupled using a NHS-EDC based in-house coupling procedure to ensure equal degrees of oligonucleotide coating on the beads.

The Luminex assay was run using a V-form microtiter plate (NUNC cat. no. 249952). 0.2 μL of each of the three beads was mixed with PCR product, hybridization buffer and sterile water to a final volumen of 100 μL. PCR product was diluted in a three-fold dilution series starting from 0.5 μL PCR product. The finale buffer consisted of 20 mM NaH$_2$PO$_4$/Na$_2$HPO$_4$, 400 mM NaCl, 0.03% Triton X-100 at pH 6.5. The plate was incubated at 35° C. for 30 minutes at a mixing speed of 900 rpm (iEMS Incubator/Shaker™ from ThermoScientific). The plate was washed three times in 5 mM NaH$_2$PO$_4$/Na$_2$HPO$_4$, 100 mM NaCl, 0.03% Triton X-100 at pH 6.5 and added detection buffer. The detection buffer consisted of 5 μg/mL Streptavidine-R-PE (Prem. Grade S-21388, Invitrogen), 100 μg/mL Albumine Fraction V (K39619718921, Merck), 20 mM NaH$_2$PO$_4$/Na$_2$HPO$_4$, 400 mM NaCl, 0.03% Triton X-100 at pH 6.5. The plate was incubated at 35° C. for 15 minutes and a mixing speed of 900 rpm and washed three times in 5 mM NaH$_2$PO$_4$/Na$_2$HPO$_4$, 100 mM NaCl, 0.03% Triton X-100 at pH 6.5 and analyzed on the Luminex200™ system counting at least 300 of each bead.

Luminex Detection of Conventional PCR Product:

The eltA PCR product was detected on the Luminex200™ system using a triplex of magnetic beads (MagPlex™) targeting eltA, estA and rrs in each well. Capture oligonucleotides for rrs were coupled to bead 13, estA to bead 15 and eltA to bead 81. Oligonucleotides were coupled to the MagPlex™ using the same protocols as for the Luminex detection of BFO modified PCR product.

| Capture oligo name: | Capture oligo sequence: |
|---|---|
| C_rrs_AD_004 | NH2-CX-HEGL-AGAGGAAGAAGAGAGAACCC CCTGG |
| C_estA_AD_005 | NH2-CX-HEGL-AAAGGAAGAGGAAAAGGCAC CCGGT |
| C_eltA_AD | NH2-CX-HEGL-AAGAGAAGGAGAAAGAGTCT CTATGTG |
| C_rrs_AD_005TT | NH2-CX-HEGL-XAGAGGAAGAAGAGAGAACC CCCTGGX |
| C_estA_AD_006 | NH2-CX-HEGL-XAAAGGAAGAGGAAAAGGCA CCCGGTX |
| C_eltA_AD_T | NH2-CX-HEGL-XAAGAGAAGGAGAAAGAGTC TCTATGTGX |

X equals para-TINA, NH2-CX equals an aminomodified cyclohexan spacer and HEGL equals a C18 hexaethyleneglycol spacer.

The Luminex assay was run using a V-form microtiter plate (NUNC cat. no. 249952). 0.2 μL of each of the three beads was mixed with PCR product, Triton X-100 (with a finale concentration of 0.03% in 100 μL reaction volumen) and sterile water to a final volumen of 80 μL. PCR product was diluted in a two-fold dilution series starting from 1.0 μL PCR product. The plate was incubated at 95° C. for five minutes on an AccuBlock™ and immediately transferred to ice for two minutes. Cold hybridization buffer was added to a total volumen of 100 μL and the finale buffer consisted of 10 mM NaH$_2$PO$_4$/Na$_2$HPO$_4$, 200 mM NaCl and 0.03% Triton X-100 at pH 6.5. The plate was incubated at 45° C. for 15 minutes at a mixing speed of 900 rpm (iEMS Incubator/Shaker™ from ThermoScientific). The plate was washed three times in 10 mM NaH$_2$PO$_4$/Na$_2$HPO$_4$, 200 mM NaCl, 0.03% Triton X-100 at pH 6.5 and added detection buffer. The detection buffer consisted of 5 μg/mL Streptavidine-R-PE (Prem. Grade S-21388, Invitrogen), 100 μg/mL Albumine Fraction V (K39619718921, Merck), 10 mM NaH$_2$PO$_4$/Na$_2$HPO$_4$, 200 mM NaCl, 0.03% Triton X-100 at pH 6.5. The plate was incubated at 45° C. for 10 minutes and a mixing speed of 900 rpm and washed three times in 10 mM NaH$_2$PO$_4$/Na$_2$HPO$_4$, 200 mM NaCl, 0.03% Triton X-100 at pH 6.5 and analyzed on the Luminex200™ system counting at least 300 of each bead.

Results:

FIG. 1 compares the detection of eltA and rrs PCR products by capture of DNA oligonucleotides and para-TINA modified DNA oligonucleotides. For both PCRs, para-TINA modified capture oligonucleotides increased the sensitivity of the Luminex detection method. Capture of denatured eltA PCR product was less sensitive than capture of BFO modified rrs PCR product. A number of factors differed between the two assays. For the detection of rrs PCR product we used 14-mer capture oligonucleotides at 35° C. for 30 minutes and a monovalent cation concentration of 420 mM, whereas eltA PCR product was detected using 27-mer capture oligonucleotides with a monovalent cation concentration of 210 mM and denaturation at 95° C. for five minutes, transfer to ice for 2 minutes (to inhibit reannealing) and incubation at 45° C. for 15 minutes (since the reannealing is likely to be complete after 15 minutes). For both assays cross-reactivity to two other capture oligonucleotides were tested and for both assays no cross-reactivity was detected.

Conclusion:

In the present experiment, the detection of BFO modified PCR product is favoured by less stringent detection condition (higher monovalent cation concentration and lower temperature) and higher target concentration (taking into account the Nanodrop™ DNA measurements and PCR fragment lengths), but on the other hand the detection of denatured PCR product is heavily favoured by capture oligonucleotides almost twice as long as the capture oligonucleotides for detection of the BFO modified PCR product. Bearing these factors in mind we conclude that the sensitivity for detection of BFO modified PCR product is significant increased compared to detection of denatured PCR product.

Example 2

We would like to show that the ortho-TINA, like the para-TINA from example 1, stops the DNA polymerase and the ortho-TINA improves the PCR reaction. We compare the ortho-TINA containing primers in the PCR reactions with a primer-pair containing a C3 spacer that stops the DNA polymerase. The used primer-pairs are shown below.

| Primer: ipaH oT mix v2oT | | | |
|---|---|---|---|
| Name | Sequences | Oligo no. | Dissolved in (µl) |
| DEC082F | GATCTAGGAGCATCTCTCGAA ZGTCCATCAGGCATCAGAAGG | 672186 | 438 |
| DEC083R | Bio-ZGGTAGACTTCTATCTC ATCCAC | 672187 | 249 |

| Primer: ipaH C3 mix | | | |
|---|---|---|---|
| Name | Sequences | Oligo no. | Dissolved in (µl) |
| DEC066F | GATCTAGGAGCATCTCTCGAA(C3) GTCCATCAGGCATCAGAAGG | 12490395 | 69 |
| DEC083R | Bio-ZGGTAGACTTCTATCTCATC CAC | 672187 | 249 |

Z is as described on page 13 wherein R is pyreneethynyl, which is substituted in the ortho position of benzene.

The DEC082F and DEC083R primers are made at DNA Technology and the DEC066F is made at EuroFins MWG Operon. The oligos are dissolved in ddH$_2$O to a concentration at 100 µM. The PCR reactions are performed at a bacterial lysate (a colony of the bacteria containing the template gene is boiled in water for 15 minutes and 1 µl of the boiled lysate is used as template in each PCR reaction). The bacterial strain used in this experiment is an *Escherichia coli*, fr1368 containing the ipaH gene. The PCR reactions are performed in a total volume of 25 µl on a SensoQuest Labcycler. The final concentrations of the components of the PCR reactions are: 1× Euro-Optima buffer (10.4 mM Tris-HCl, 56.8 mM Trizma-base, 16.1 mM (NH)$_4$SO$_4$, 0.01% Tween 80, 30 mM NaCl), 2 mM dATP, dGTP, dCTP and 0.66 mM dTTP and 1.33 mM dUTP, 2.5 mM MgCl$_2$, 0.08% BSA, 1×SYBR green I, 0.25 U Uracil DNA glycosylase (Fermantas) and 1 U KAPA2G Robust HS DNA polymerase (KAPA-Biosystems). Four different primer concentrations are used, 50 nM, 100 nM, 200 nM and 400 nM. The PCR reactions are tested with an annealing-gradient from 60 to 80° C. The PCR program is shown below.

PCR Program Euro Optima Mastermix:

| Step | Temp (° C.) | Time |
|---|---|---|
| Initial denaturation | 95° C. | 4 min |
| 30 cycles of: | | |
| Denaturation | 95° C. | 15 sec |
| Annealing | 70° C. +/− 10° C. | 30 sec |
| Extension | 72° C. | 30 sec |
| Finale extension | 72° C. | 1 min |

The plate setup and the precise annealing gradient is shown below.

| | 1 | 2 | 3 | 4 | 5 | 6 | 7 | 8 | 9 | 10 | 11 | 12 |
|---|---|---|---|---|---|---|---|---|---|---|---|---|
| | | | | | | ° C. | | | | | | |
| | 60.0 | 61.8 | 63.6 | 65.5 | 67.3 | 69.1 | 70.9 | 72.7 | 74.5 | 76.4 | 78.2 | 80.0 |
| A | | | | | | 50 nM ipaH oT mix v2oT | | | | | | |
| B | | | | | | 50 nM ipaH C3 mix | | | | | | |
| C | | | | | | 100 nM ipaH oT mix v2oT | | | | | | |
| D | | | | | | 100 nM ipaH C3 mix | | | | | | |
| E | | | | | | 200 nM ipaH oT mix v2oT | | | | | | |
| F | | | | | | 200 nM ipaH C3 mix | | | | | | |
| G | | | | | | 400 nM ipaH oT mix v2oT | | | | | | |
| H | | | | | | 400 nM iaH C3 mix | | | | | | |

The PCR products are tested on agarose-gels for comparison. 5 µl of each PCR product is tested on the gels. The 2,5% agarose-gels with Gel Red ran at 130 volt (constant) for 20 minutes. Lane 1 contains 1 µl molecule marker (GeneRuler 100 bp Plus DNA Ladder (Fermentas, SM0323)). Lane 2-12 contains the PCR products from column 2-12. Each gel contains the two types of PCR reactions at the same concentration. The ortho-TINA containing PCR reactions are always loaded first (row 1) followed by the C3 spacer PCR reactions (row2).

Results:

FIG. 4A shows the ortho-TINA (row 1) and C3 spacer PCR (row 2) products at 50 nM on the annealing-gradient. Both ortho-TINA PCR reactions and the C3 spacer PCR reactions perform from 61.8° C. to 70.9° C. and 67.3° C. respectively, showing that the ortho-TINA PCR reactions perform better than the C3 spacer reactions at 50 nM primer concentration.

FIG. 4B shows the ortho-TINA (row 1) and C3 spacer PCR (row 2) products at 100 nM on the annealing-gradient. Both ortho-TINA PCR reactions and the C3 spacer PCR reactions perform from 61.8° C. to 72.7° C. and 69.1° C. respectively, showing that the ortho-TINA PCR reactions perform better than the C3 spacer reactions at 100 nM primer concentration.

FIG. 5A shows the ortho-TINA (row 1) and C3 spacer PCR (row 2) products at 200 nM on the annealing-gradient. Both ortho-TINA PCR reactions and the C3 spacer PCR reactions perform from 61.8° C. to 80.0° C. and 70.9° C. respectively, showing that the ortho-TINA PCR reactions perform better than the C3 spacer reactions at 200 nM primer concentration. Even though the last PCR reactions for the ortho-TINA only generate weak bands.

FIG. 5B shows the ortho-TINA (row 1) and C3 spacer PCR (row 2) products at 400 nM on the annealing-gradient. Both ortho-TINA PCR reactions and the C3 spacer PCR reactions perform from 61.8° C. to 80.0° C. and 72.7° C. respectively, showing that the ortho-TINA PCR reactions perform better than the C3 spacer reactions at 400 nM primer concentration.

Overall conclusion of the PCR results including the ortho-TINA and C3 spacer primers. The ortho-TINA primers perform generally better than the C3 spacer containing primers. The ortho-TINA primers perform at higher annealing-temperatures than the C3 spacer primers at all tested concentrations. This means that ortho-TINA primers can be used at lower concentrations and perform as good as the C3 spacer containing primers or ortho-TINA containing primers can be used at a higher annealing-temperature and perform as good as the C3 spacer primers. This leads to a great advantage in multiplex PCR, since the primer concentration can be reduced and the annealing-temperature can be raised with a better result.

The next step is to show that the ortho-TINA in the Cliff-Hanger primer can stop the DNA polymerase and thereby generate the single-stranded overhang. To test the ability of the ortho-TINA to stop the DNA polymerase we make a capture study of the PCR products on Luminex beads coated with single-stranded oligos. If the ortho-TINA has the ability to stop the DNA polymerase and generate the single-stranded overhang, it will be possible to capture the ortho-TINA fragments on the Luminex beads at least as good as the C3 spacer fragments.

To the Luminex capture test we use 1 µl of purified PCR fragment compared to the agarose-gel analysis where we used 5 µl of PCR product. We have selected 4 annealing-temperatures from the 400 nM experiment, from where the PCR products are purified (see below).

The PCR fragments are purified with the MN Nucleospin Extract II kit (Macherey-Nagel) in accordance with the protocol. To keep the track and trace in the experiments, the purified PCR products are eluted in the same volume as the starting volume.

The Luminex capture analysis is performed as: 1 µl of purified PCR product are diluted 3-fold 6 times to generate a dilution-serie (1; 0.3333; 0.1111; 0.0370; 0.0123; 0.0041; 0.0014 µl). The PCR products are analysed in HB-buffer with a final concentration of 20 mM $NaH_2PO_4/Na_2HPO_4$+400 mM NaCl+0.03% Triton x-100, pH 6.94 and in the presents a luminex beads with the capture oligo (0.2 µl per well). The capture mix is incubated at 51° C. and 900 rpm for 30 minutes. After the incubation the reactions are washed 3 times with wash-buffer (HB-buffer diluted 4 times). After the last wash the detection mix is added to the reactions and it consists of 100 µg/ml Albumin fraction V (Merck) and 5 µg/ml Streptavidin-R-PhycoErythrin (Sigma) in wash-buffer. The detection mix is incubated at 51° C. and 900 rpm for 15 minutes followed by 3 washes with wash-buffer. The Luminex instrument is programmed to count 300 beads per well over 90 seconds.

Results.

Figure 6:
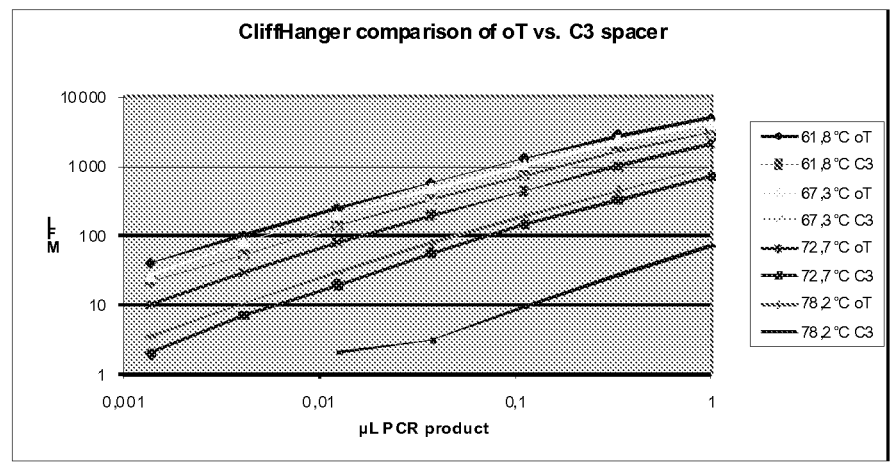
FIG. 6 shows results from Luminex capture analysis of ortho-TINA and C3 spacer modified bifunctional oligonucleotides. See example 2 for details.

The results from the capture analysis (FIG. 6) show that the ortho-TINA PCR products can be captured, so this means that the ortho-TINA can stop the DNA polymerase and generate the single-stranded overhang. The Luminex results reflect the results from the agarose-gel analysis. The ortho-TINA PCR products seems to have a higher concentration on the agarose-gels than the C3 spacer products and in the Luminex analysis the ortho-TINA also generates a higher MFI than the C3 spacer products. This shows that the ortho-TINA stops the DNA polymerase at least as good as the C3 spacer. The MFI correlates with the intensity of the bands of the PCR products on the agarose-gels. The Luminex assay seems also to be more sensitive than the agarose-gels, since we can detect down to 0.0014 µl PCR product (the dilution curve has a nice linearity). On the agarose-gels the difference between the two types of primers is approximately 3° C., whereas in the Luminex analysis it is approximately 6° C. showing that the Luminex instrument is more sensitive and can discriminate better than a agarose-gel.

Final Conclusion.

We have showed that the ortho-TINA improves the PCR reaction compared to a C3 spacer and that it also can stop the DNA polymerase at least as good as the C3 spacer.

| | 1 | 2 | 3 | 4 | 5 | 6 | 7 | 8 | 9 | 10 | 11 | 12 |
|---|---|---|---|---|---|---|---|---|---|---|---|---|
| | | | | | | ° C. | | | | | | |
| | 60.0 | 61.8 | 63.6 | 65.5 | 67.3 | 69.1 | 70.9 | 72.7 | 74.5 | 76.4 | 78.2 | 80.0 |
| G | | x | | x | | x | | x | | | | |
| H | | x | | x | | x | | x | | | | |

The invention claimed is:

1. A method comprising the steps of:
   a. Providing a template nucleic acid
   b. Providing a bifunctional oligonucleotide (bfo) comprising a primer/template (pt) region (complementary to part of the template nucleic acid) in its 3'end and a capture region (cr), wherein the pt region and the cr region is separated by a polymerase block (B)
   c. Mixing the components of steps a-b and providing conditions that allow the pt region of the bfo to anneal to the template nucleic acid and the B to improve the production of amplified template nucleic acid d. Under conditions allowing primer extension, extending the pt region of the bfo
e. Thereby generating a double stranded nucleic acid with a single stranded overhang (dso) corresponding to the cr region of the bfo
wherein the polymerase block (B) is a TINA monomer that can be described by the formula:

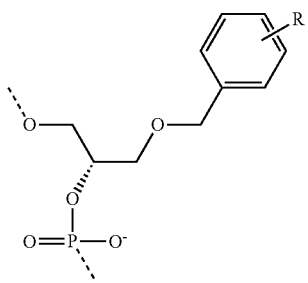

wherein R is selected from the group consisting of arylethynyl, pyreneethynyl, and 1H-phenanthro[9,10-d]imidazol-2-yl.

2. The method of claim 1 further comprising the steps of
f. Providing a second primer, which is complementary to the first extension product of step d
g. Denaturing the product of the step d
h. Under conditions allowing primer extension, extending the second primer annealed to the first extension product.

3. The method of claim 2 comprising a second primer set for multiplex PCR.

4. The method of claim 3 further comprising a capture step, wherein the capture region (cr) of the dso is annealed to a capture probe.

5. The method of claim 4, wherein the capture probe is immobilized on a solid support or alternatively is adapted for immobilization on a solid support.

6. The method of claim 5, further comprising a fractionation step to separate annealed molecules from non-annealed molecules.

7. The method of claim 6, wherein the capture probe comprises an intercalator.

8. The method of claim 7, wherein the intercalator is a TINA monomer as described by the formula:

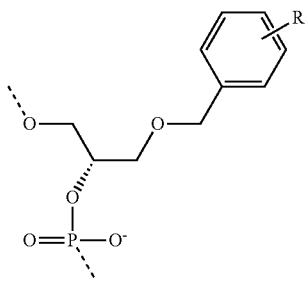

wherein R is selected from the group consisting of arylethynyl, pyreneethynyl, and 1H-phenanthro[9,10-d]imidazol-2-yl.

9. The method of claim 4, wherein the capture probe comprises an intercalator.

10. The method of claim 5, wherein the capture probe comprises an intercalator.

11. The method of claim 10, wherein the intercalator is a TINA monomer as described by the formula:

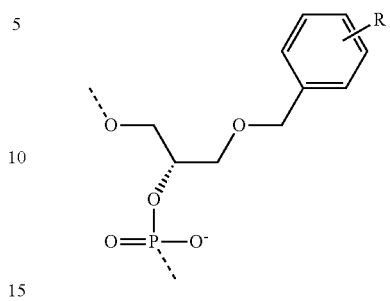

wherein R is selected from the group consisting of arylethynyl, pyreneethynyl, and 1H-phenanthro[9,10-d]imidazol-2-yl.

12. The method of claim 9, wherein the intercalator is a TINA monomer as described by the formula:

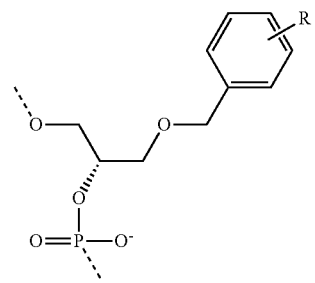

wherein R is selected from the group consisting of arylethynyl, pyreneethynyl, and 1H-phenanthro[9,10-d]imidazol-2-yl.

13. The method of claim 4 further comprising
a. a detection phase, whereby the dso annealed to the capture probe is visualized and/or
b. a purification phase, whereby the dso annealed to the capture probe is purified and/or
c. a manipulation phase, whereby the dso annealed to the capture probe is further manipulated.

14. The method of claim 5 further comprising
a. a detection phase, whereby the dso annealed to the capture probe is visualized and/or
b. a purification phase, whereby the dso annealed to the capture probe is purified and/or
c. a manipulation phase, whereby the dso annealed to the capture probe is further manipulated.

15. The method of claim 6 further comprising
a. a detection phase, whereby the dso annealed to the capture probe is visualized and/or
b. a purification phase, whereby the dso annealed to the capture probe is purified and/or
c. a manipulation phase, whereby the dso annealed to the capture probe is further manipulated.

16. The method of claim 7 further comprising
a. a detection phase, whereby the dso annealed to the capture probe is visualized and/or
b. a purification phase, whereby the dso annealed to the capture probe is purified and/or
c. a manipulation phase, whereby the dso annealed to the capture probe is further manipulated.

17. The method of claim 8 further comprising
a. a detection phase, whereby the dso annealed to the capture probe is visualized and/or
b. a purification phase, whereby the dso annealed to the capture probe is purified and/or
c. a manipulation phase, whereby the dso annealed to the capture probe is further manipulated.

18. The method of claim 1 comprising a second primer set for multiplex PCR.

19. The method of claim 1 further comprising a capture step, wherein the capture region (cr) of the dso is annealed to a capture probe.

* * * * *

SEQUENCE LISTING

<160> NUMBER OF SEQ ID NOS: 19

<210> SEQ ID NO 1
<211> LENGTH: 37
<212> TYPE: DNA
<213> ORGANISM: Artificial Sequence
<220> FEATURE:
<223> OTHER INFORMATION: Oligonucleotide

<400> SEQUENCE: 1
aagagaagga gaaagagtct ctatgtgcat acggagc                             37

<210> SEQ ID NO 2
<211> LENGTH: 19
<212> TYPE: DNA
<213> ORGANISM: Artificial Sequence
<220> FEATURE:
<223> OTHER INFORMATION: Oligonucleotide

<400> SEQUENCE: 2
ccatactgat tgccgcaat                                                 19

<210> SEQ ID NO 3
<211> LENGTH: 37
<212> TYPE: DNA
<213> ORGANISM: Artificial Sequence
<220> FEATURE:
<223> OTHER INFORMATION: Oligonucleotide

<400> SEQUENCE: 3
agaggaagaa gagagaaccc cctggacgaa gactgac                             37

<210> SEQ ID NO 4
<211> LENGTH: 20
<212> TYPE: DNA
<213> ORGANISM: Artificial Sequence
<220> FEATURE:
<223> OTHER INFORMATION: Oligonucleotide

<400> SEQUENCE: 4
accgctggca acaaaggata                                                20

<210> SEQ ID NO 5
<211> LENGTH: 14
<212> TYPE: DNA
<213> ORGANISM: Artificial Sequence
<220> FEATURE:
<223> OTHER INFORMATION: Oligonucleotide

<400> SEQUENCE: 5
tttcctcttc cttt                                                      14

<210> SEQ ID NO 6
<211> LENGTH: 14
<212> TYPE: DNA
<213> ORGANISM: Artificial Sequence
<220> FEATURE:
<223> OTHER INFORMATION: Oligonucleotide

<400> SEQUENCE: 6
tctcttcttc ctct                                                      14

<210> SEQ ID NO 7
<211> LENGTH: 14
<212> TYPE: DNA
<213> ORGANISM: Artificial Sequence

```
<220> FEATURE:
<223> OTHER INFORMATION: Oligonucleotide

<400> SEQUENCE: 7
tttctccttc tctt                                                    14

<210> SEQ ID NO 8
<211> LENGTH: 14
<212> TYPE: DNA
<213> ORGANISM: Artificial Sequence
<220> FEATURE:
<223> OTHER INFORMATION: Oligonucleotide

<400> SEQUENCE: 8
tttcctcttc cttt                                                    14

<210> SEQ ID NO 9
<211> LENGTH: 14
<212> TYPE: DNA
<213> ORGANISM: Artificial Sequence
<220> FEATURE:
<223> OTHER INFORMATION: Oligonucleotide

<400> SEQUENCE: 9
tctcttcttc ctct                                                    14

<210> SEQ ID NO 10
<211> LENGTH: 14
<212> TYPE: DNA
<213> ORGANISM: Artificial Sequence
<220> FEATURE:
<223> OTHER INFORMATION: Oligonucleotide

<400> SEQUENCE: 10
tttctccttc tctt                                                    14

<210> SEQ ID NO 11
<211> LENGTH: 25
<212> TYPE: DNA
<213> ORGANISM: Artificial Sequence
<220> FEATURE:
<223> OTHER INFORMATION: Oligonucleotide

<400> SEQUENCE: 11
agaggaagaa gagagaaccc cctgg                                        25

<210> SEQ ID NO 12
<211> LENGTH: 25
<212> TYPE: DNA
<213> ORGANISM: Artificial Sequence
<220> FEATURE:
<223> OTHER INFORMATION: Oligonucleotide

<400> SEQUENCE: 12
aaaggaagag gaaaaggcac ccggt                                        25

<210> SEQ ID NO 13
<211> LENGTH: 27
<212> TYPE: DNA
<213> ORGANISM: Artificial Sequence
<220> FEATURE:
<223> OTHER INFORMATION: Oligonucleotide

<400> SEQUENCE: 13
aagagaagga gaaagagtct ctatgtg                                      27
```

```
<210> SEQ ID NO 14
<211> LENGTH: 25
<212> TYPE: DNA
<213> ORGANISM: Artificial Sequence
<220> FEATURE:
<223> OTHER INFORMATION: Oligonucleotide

<400> SEQUENCE: 14
agaggaagaa gagagaaccc cctgg                                          25

<210> SEQ ID NO 15
<211> LENGTH: 25
<212> TYPE: DNA
<213> ORGANISM: Artificial Sequence
<220> FEATURE:
<223> OTHER INFORMATION: Oligonucleotide

<400> SEQUENCE: 15
aaaggaagag gaaaaggcac ccggt                                          25

<210> SEQ ID NO 16
<211> LENGTH: 27
<212> TYPE: DNA
<213> ORGANISM: Artificial Sequence
<220> FEATURE:
<223> OTHER INFORMATION: Oligonucleotide

<400> SEQUENCE: 16
aagagaagga gaaagagtct ctatgtg                                        27

<210> SEQ ID NO 17
<211> LENGTH: 41
<212> TYPE: DNA
<213> ORGANISM: Artificial Sequence
<220> FEATURE:
<223> OTHER INFORMATION: Oligonucleotide

<400> SEQUENCE: 17
gatctaggag catctctcga agtccatcag gcatcagaag g                        41

<210> SEQ ID NO 18
<211> LENGTH: 22
<212> TYPE: DNA
<213> ORGANISM: Artificial Sequence
<220> FEATURE:
<223> OTHER INFORMATION: Oligonucleotide

<400> SEQUENCE: 18
ggtagacttc tatctcatcc ac                                             22

<210> SEQ ID NO 19
<211> LENGTH: 41
<212> TYPE: DNA
<213> ORGANISM: Artificial Sequence
<220> FEATURE:
<223> OTHER INFORMATION: Oligonucleotide

<400> SEQUENCE: 19
gatctaggag catctctcga agtccatcag gcatcagaag g                        41
```